(12) United States Patent
Kelley et al.

(10) Patent No.: US 11,497,647 B2
(45) Date of Patent: Nov. 15, 2022

(54) ANATOMICAL SUPPORT SYSTEMS, DEVICES, AND RELATED METHODS

(71) Applicant: Emory University, Atlanta, GA (US)

(72) Inventors: Robert Kelley, Avondale Estates, GA (US); Sruti Bheri, Atlanta, GA (US); Esther Max-Onakpoya, Lexington, KY (US); Xiaoshan Shao, Baltimore, MD (US); Alena Sim, Irvine, CA (US)

(73) Assignee: Emory University, Atlanta, GA (US)

( * ) Notice: Subject to any disclaimer, the term of this patent is extended or adjusted under 35 U.S.C. 154(b) by 821 days.

(21) Appl. No.: 16/393,634

(22) Filed: Apr. 24, 2019

(65) Prior Publication Data

US 2019/0321215 A1    Oct. 24, 2019

Related U.S. Application Data

(60) Provisional application No. 62/662,086, filed on Apr. 24, 2018.

(51) Int. Cl.
| | | |
|---|---|---|
| *A61F 6/08* | (2006.01) | |
| *A61F 6/16* | (2006.01) | |
| *A61B 17/42* | (2006.01) | |
| *A61F 2/00* | (2006.01) | |

(52) U.S. Cl.
CPC ............... *A61F 6/08* (2013.01); *A61B 17/42* (2013.01); *A61F 2/0004* (2013.01)

(58) Field of Classification Search
CPC ...... A61F 6/08; A61F 6/12; A61F 6/14; A61F 6/16; A61F 2/0004; A61F 2/02; A61F 6/146; A61B 17/42
See application file for complete search history.

(56) References Cited

U.S. PATENT DOCUMENTS

| | | | |
|---|---|---|---|
| 1,590,124 A | | 9/1897 | Wilson |
| 2,365,296 A | | 12/1944 | Schimpf |
| 4,381,771 A | * | 5/1983 | Gabbay .................. A61F 6/08 128/836 |
| 5,611,768 A | | 3/1997 | Tutrone, Jr. |
| 5,947,991 A | | 9/1999 | Cowan |

(Continued)

FOREIGN PATENT DOCUMENTS

| | | |
|---|---|---|
| WO | WO2017152029 | 9/2017 |
| WO | WO2017020892 | 2/2018 |
| WO | WO2018031515 | 2/2018 |

*Primary Examiner* — Camtu T Nguyen
(74) *Attorney, Agent, or Firm* — Emory Patent Group

(57) ABSTRACT

The systems, devices and methods provide customizable and adjustable support to anatomical tissue or organs, such as pelvic, vaginal, uterine, cervical, bladder, rectal, among others, or any combination thereof. The anatomical support device may include a support member having a periphery that surrounds an opening. The support member may be configured to releasably and adjustably expand between one or more expanding states from a resting state and contract to the resting state. The support member may include a first portion and a second portion disposed along the periphery. Each portion may include a passage cross-sectional area and a wall thickness. The first wall thickness and/or the first passage cross-sectional area of the first portion may be different from the second wall thickness and/or the second passage cross-sectional area of the second portion.

17 Claims, 11 Drawing Sheets

(56) References Cited

U.S. PATENT DOCUMENTS

| | | |
|---|---|---|
| 7,105,007 B2 | 9/2006 | Hibler |
| 8,403,937 B2 | 3/2013 | Schwardt et al. |
| 2007/0062541 A1 | 3/2007 | Zhou et al. |
| 2008/0319472 A1 | 12/2008 | Shelley |
| 2009/0266367 A1 | 10/2009 | Ziv et al. |
| 2012/0259159 A1 | 10/2012 | Karapasha |
| 2013/0158340 A1 | 6/2013 | Altan et al. |
| 2014/0083433 A1 | 3/2014 | Lowry |
| 2016/0089380 A1 | 3/2016 | Black et al. |
| 2016/0250229 A1 | 9/2016 | Campos Perez et al. |
| 2017/0304038 A1 | 10/2017 | Albrecht et al. |
| 2018/0001066 A1 | 1/2018 | Cline et al. |

\* cited by examiner

ANATOMICAL SUPPORT SYSTEMS, DEVICES, AND RELATED METHODS

CROSS-REFERENCE TO RELATED APPLICATION

This application claims the benefit of U.S. Provisional Application No. 62/662,086 filed Apr. 24, 2018. The entirety of this application is hereby incorporated by reference for all purposes.

BACKGROUND

Intra-vaginal devices, such as pessaries, have been used to stabilize surrounding anatomy to treat various gynecological, pelvic and gastric issues, such as cervical incompetence, pelvic organ prolapse, fecal or urinary incontinence, among others. However, these devices have generally been not customizable or adjustable to the patient's anatomy, leading to improper fit and unsatisfactory outcomes, such as complications. For example, for cervical incompetence, the improper fit can result in potential cervical rupture, as well as miscarriage or premature birth.

SUMMARY

Thus, there is need for systems, devices, and methods that provide a customizable, adjustable fit so that it can properly provide anatomical support and reduce complications.

The disclosure relates to systems, devices, and methods that can provide customizable and adjustable support to anatomical tissue or organs, such as pelvic, vaginal, uterine, cervical, bladder, rectal, among others, or any combination thereof.

In some embodiments, the devices may include an anatomical support device. In some embodiments, the device may include an opening and a support member having a periphery that surrounds the opening. The support member may be configured to releasably and adjustably expand between one or more expanding states from a resting state and contract to the resting state. In some embodiments, the support member may include an internal passage that extends along the periphery and one or more portions disposed along the periphery. The one or more portions may include a first portion disposed along the periphery and a second portion disposed along the periphery. The internal passage along the first portion may have a first passage cross-sectional area and the first portion may have a first wall thickness along the periphery. The internal passage along the second portion may have a second passage cross-sectional area and the second portion may have a second wall thickness along the periphery. The first wall thickness and/or the first passage cross-sectional area may be different from the second wall thickness and/or the second passage cross-sectional area.

In some embodiments, the first wall thickness may be greater than the second wall thickness. The second portion may be larger than the first portion when expanded.

In some embodiments, the first passage cross-sectional area may be smaller than the second passage cross-sectional area. The second portion may be larger than the first portion when in the one or more expanded states.

In some embodiments, the first passage cross-sectional area may be defined by a first passage cross-sectional height and a first passage cross-sectional width. The second passage cross-sectional area may be defined by a second passage cross-sectional height and a second passage cross-sectional width. In some embodiments, the first passage cross-sectional height and/or the first passage cross-sectional width may be different from the second passage cross-sectional height and/or the second passage cross-sectional passage width.

In some embodiments, the support member may further include one or more mid portions disposed between the first portion and the second portion.

In some embodiments, the second portion may be structured to expand faster than the first portion when expanding to the one or more expanded states.

In some embodiments, the device may further include an adapter disposed on one portion of the one or more portions. The adapter may be in communication with the internal passage and configured to receive tubing. The adapter may include a valve. The valve may be configured to open so that the support member expands and/or contracts and to close so that the support member maintains the one or more expanding states and/or the resting state.

In some embodiments, the support member may have a center relative to the periphery and the opening may be disposed offset from the center.

In some embodiments, the internal passage may be configured to receive a fluid. The one or more expanded states may be based on the amount of fluid disposed within the internal passage.

In some embodiments, the support member may be made of one or more flexible materials.

In some embodiments, the support member may be structured to be collapsible when the support member may be in the resting state.

In some embodiments, the device may further include a base member that protrudes from the support member and envelopes the opening. The base member may include one or more openings. In some embodiments, the base member may be structured to be non-expandable.

In some embodiments, an anatomical device may include an opening and a support member having a periphery surrounding the opening. The periphery may include an outer surface and an inner surface. In some embodiments, the support member may be configured to releasably and adjustably expand between one or more expanding states from a resting state and contract to the resting state. The support member may include an internal passage disposed along the periphery. The inner surface may surround the internal passage. The support member may further include a wall thickness defined by the outer surface and the inner surface. The support member may include one or more portions disposed along the periphery. In some embodiments, the one or more portions may include a first portion and a second portion disposed along the periphery. The first portion may have a first cross-sectional area. The first cross-sectional area may include a first wall thickness and a first passage cross-sectional area. The second portion may have a second cross-sectional area. The second cross-sectional area may include a second wall thickness and a second passage cross-sectional area. In some embodiments, the first cross-sectional area may be different from the second cross-sectional area, and the first portion and the second portion may be structured to expand to a different size when expanded in each of the one or more expanding states.

In some embodiments, the support member may have a center relative to the periphery and the opening may be disposed offset from the center.

In some embodiments, the first wall thickness may be greater than the second wall thickness and the second portion may have a larger cross-sectional area than the first portion when expanded.

In some embodiments, the first cross-sectional area may be based on a first cross-sectional height and a first cross-sectional width and the second cross-sectional area may be based on a second cross-sectional height and a second cross-sectional width. In some embodiments, the first cross-sectional height and/or the first cross-sectional width may be smaller than the second cross-sectional height and/or the second cross-sectional width.

In some embodiments, the device may further include a base member that protrudes from the outer surface and envelopes the opening. The base member may include one or more openings. In some embodiments, the base member may be structured to be non-expandable.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
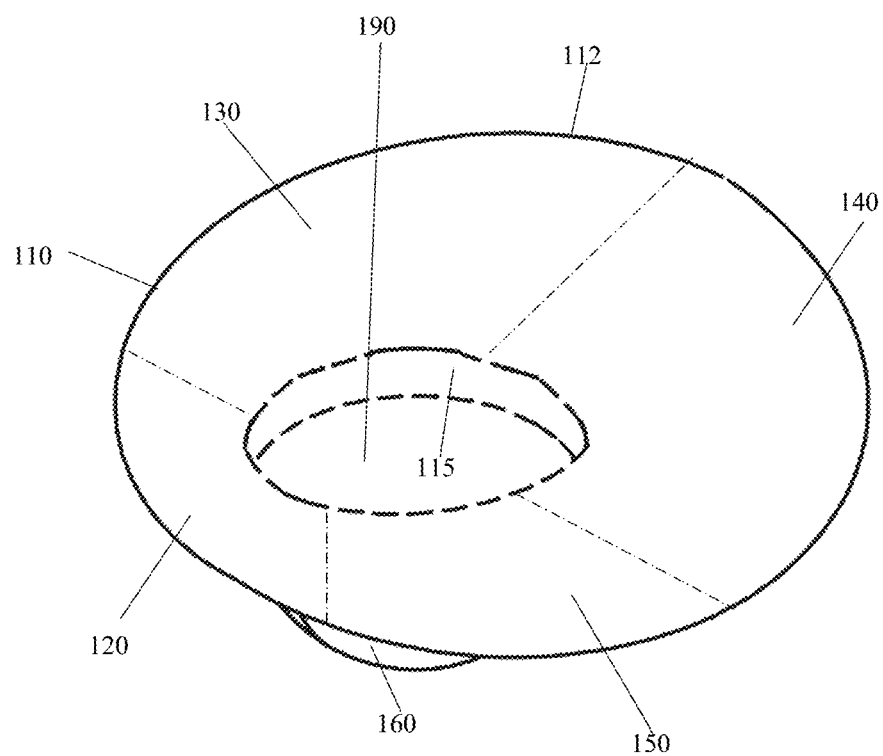
FIG. 1 shows a top perspective view of an anatomical support device according to embodiments.
Figure 2:
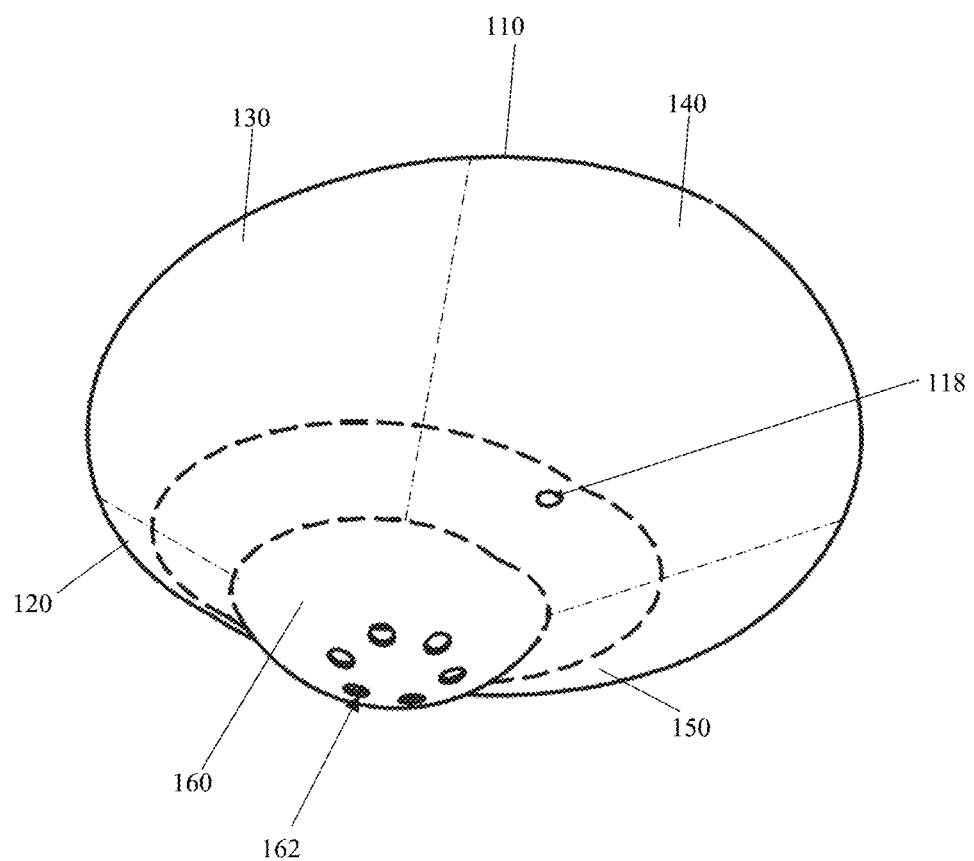
FIG. 2 shows a bottom perspective view of the device shown in FIG. 1.
Figure 3:
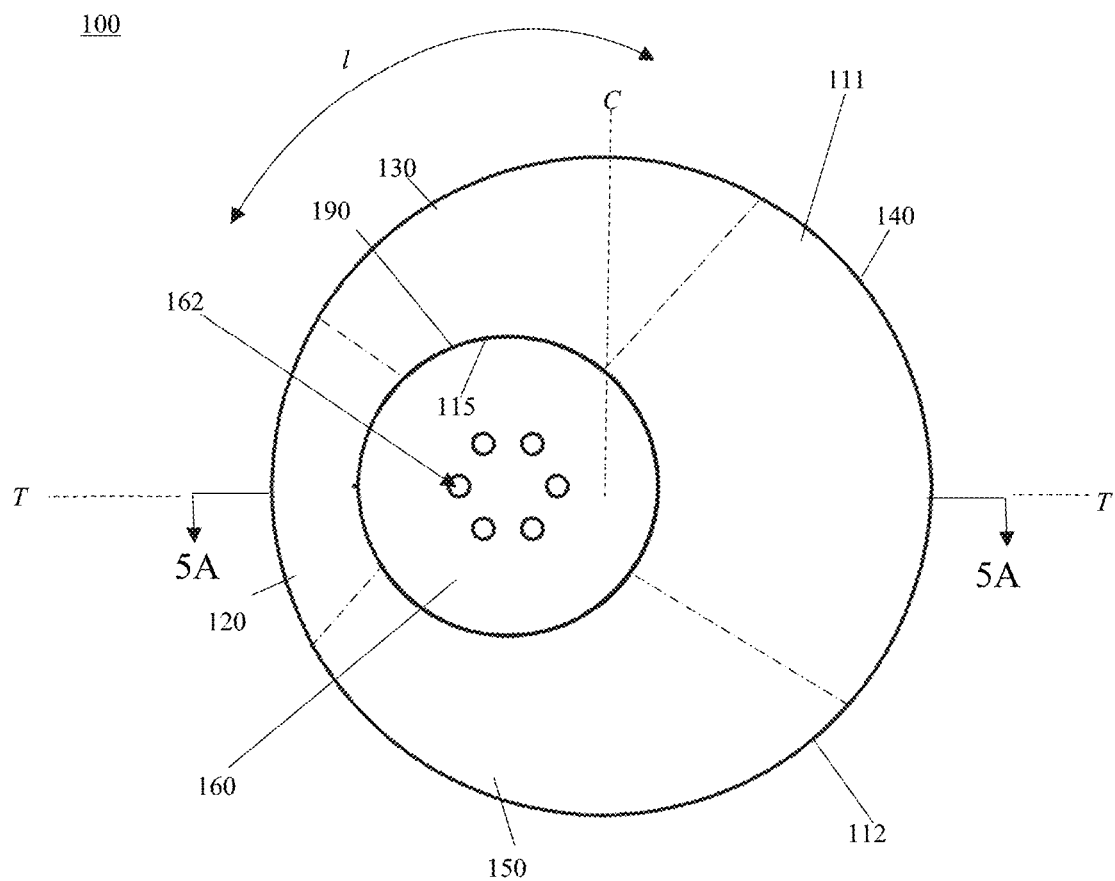
FIG. 3 shows a top view of the device shown in FIG. 1.
Figure 4:
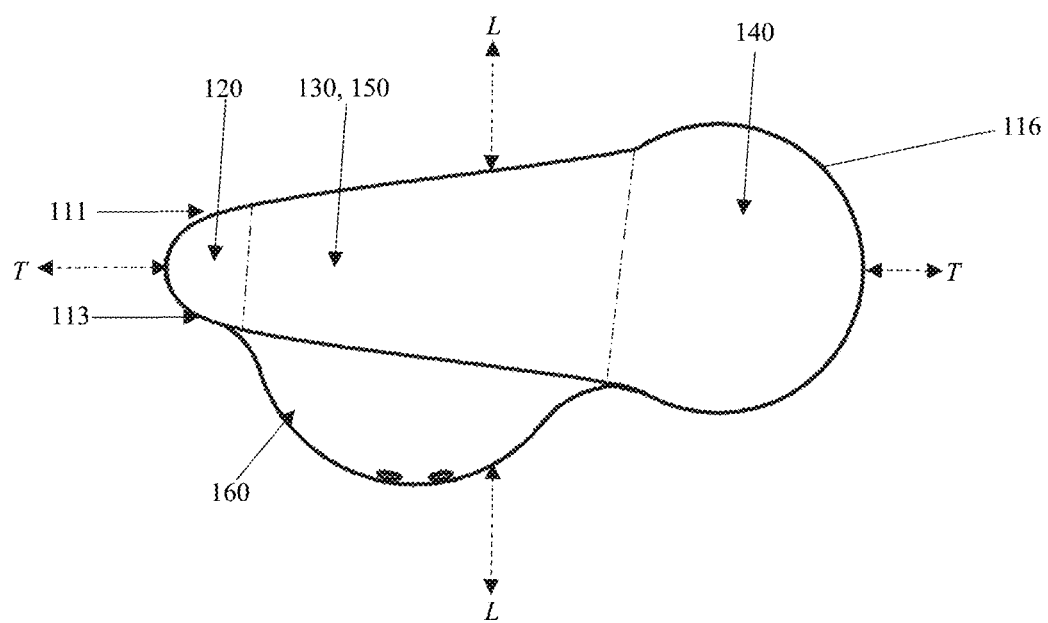
FIG. 4 shows a side view of the device shown in FIG. 1.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems, devices and methods according to the disclosure can provide support to anatomical tissue or organs, such as pelvic, vaginal, uterine, cervical, bladder, rectal, among others, or any combination thereof. The devices can be configured to be customizable so as to accommodate different anatomies and mechanical properties. For example, the devices according to the disclosure can be configured to be releasably and adjustably expanded to different levels or states of expansion, by a user (e.g., a clinician and/or the patient), to fit the patient's anatomy (e.g., the vaginal canal) at time of insertion as well as during the course of treatment (e.g., changes in cervix over a pregnancy). The adjustable and customizable nature of the devices can thereby reduce the issues of fitting without requiring multiple device sizes. The devices can also be structured so that the maximum expansion prevents significant damage to the surrounding tissue (e.g., rupture of the vaginal tissue). The devices can therefore provide a secure fit with substantially no displacement and minimal discomfort. The systems and devices can also be configured for non-invasive insertion methods in an outpatient setting.

The devices, systems, and methods are described with respect to supporting vaginal/cervical tissue to treat cervical incompetence. The devices and methods can be configured to wrap around the cervix to ensure the closure and maintain its position around the cervix by its positioning against the vaginal wall when expanded. However, it will be understood that the devices, systems, and methods can be configured to support the same region and/or other regions to treat other conditions, including but not limited to pelvic organ prolapse, incontinence (e.g., fecal incontinence, urinary incontinence, etc.), vaginal prolapse, among others, or any combination thereof.

Figure 5A:
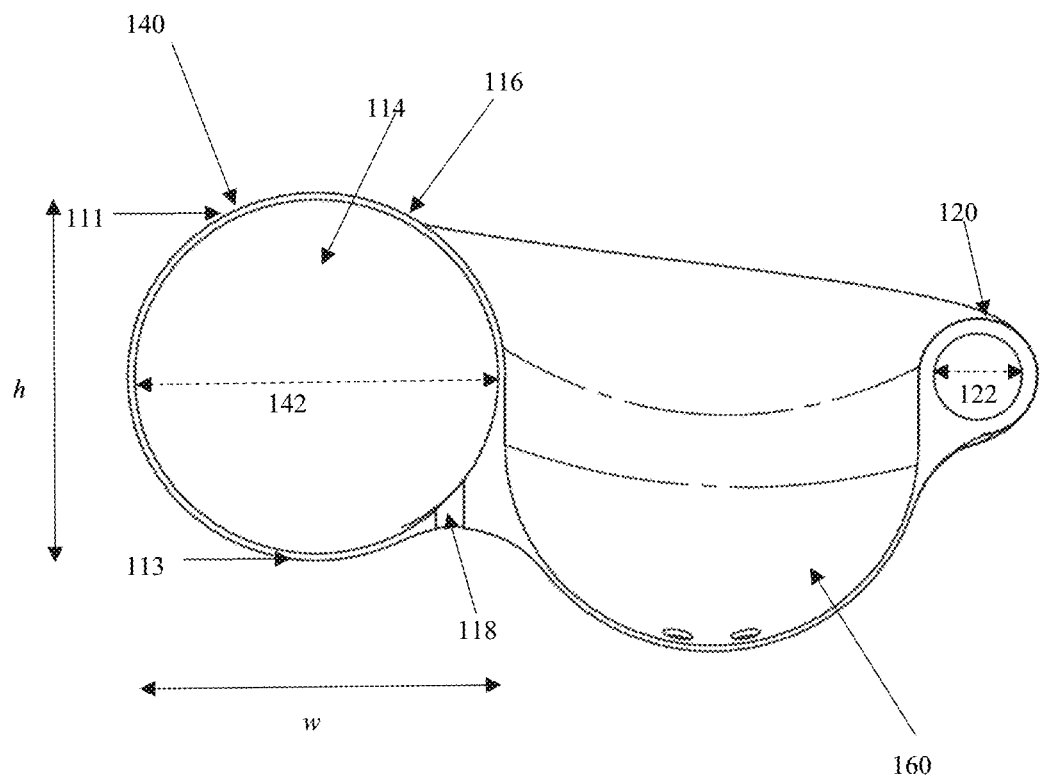
FIG. 5A-C show cross-sectional views of the device shown in FIG. 1.
Figure 5B:
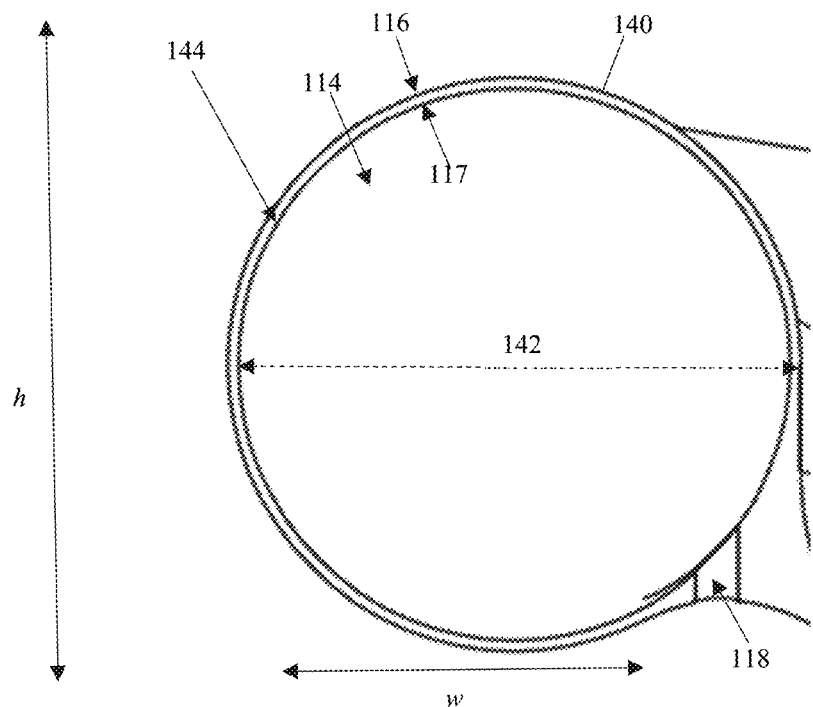
Figure 5C:
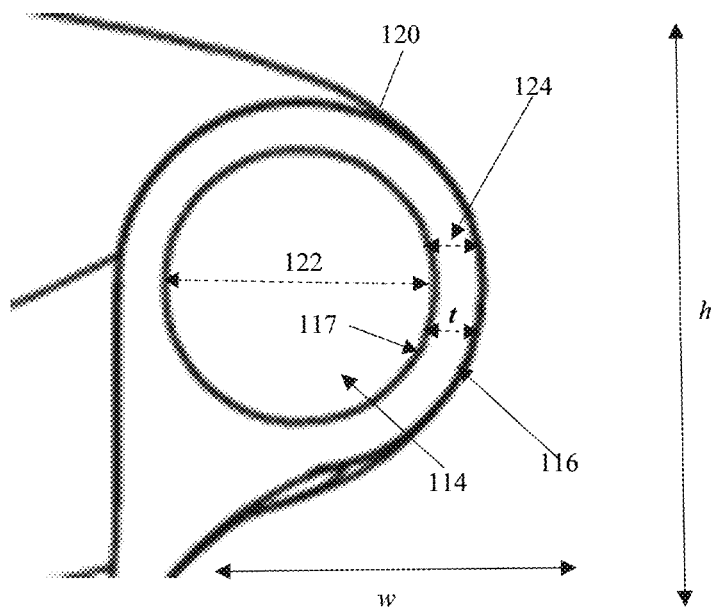
Figure 6:
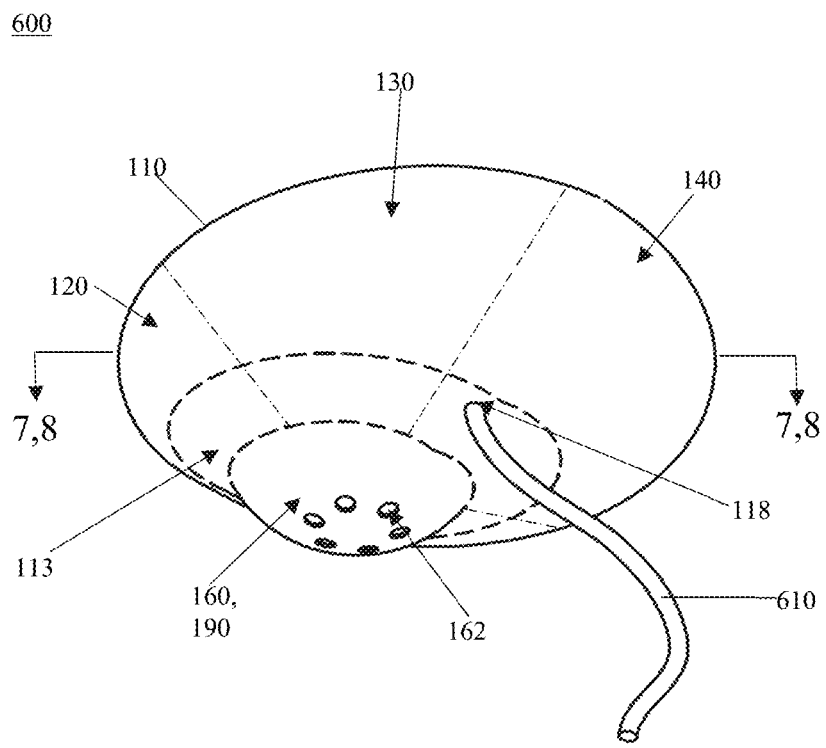
FIG. 6 shows a bottom perspective view of an anatomical support device system that includes the anatomical support device according to embodiments.
Figure 7:
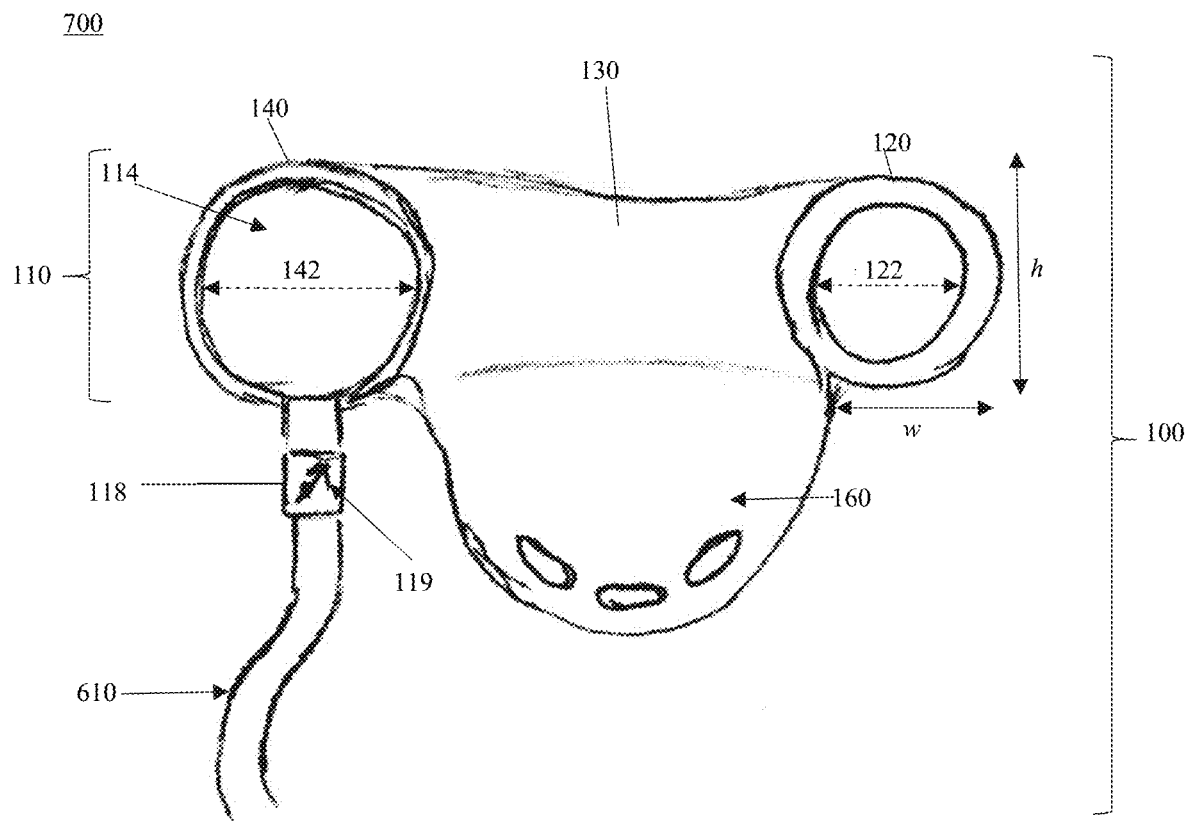
FIG. 7 shows a cross-sectional view of the device shown in FIG. 6 in resting, deflated state.
Figure 8:
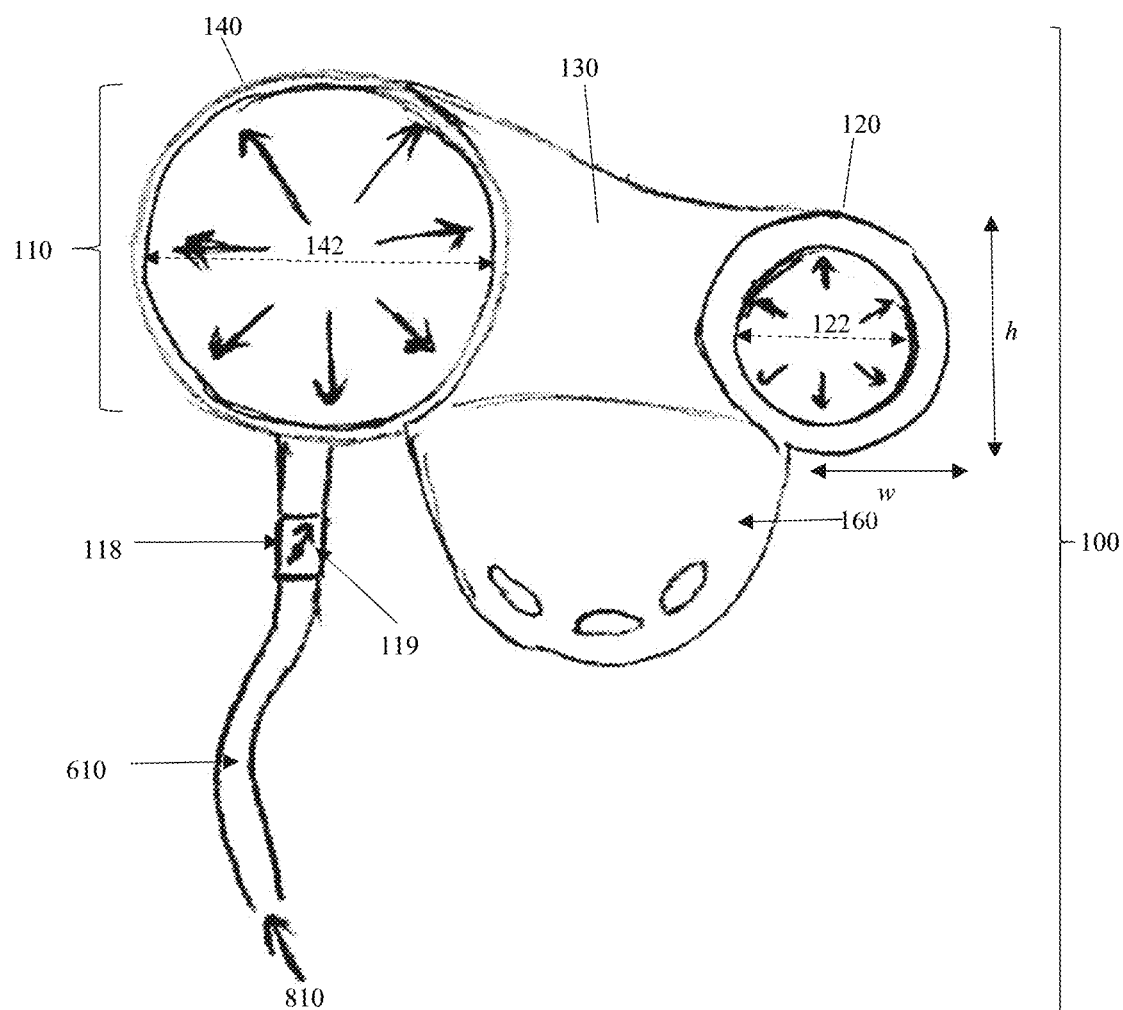
FIG. 8 shows a cross-sectional view of the device shown in FIG. 6 in an expanded state.

FIGS. 1-5 show views of an example of an anatomical support device 100 and FIGS. 6-8 show views of an example of a system 600 that includes the support device 100. In some embodiments, the device 100 may include a support member 110 that is configured to be expandable. In some embodiments, the device 100 may include an opening 190. The support member 110 may be configured to surround the opening 190. The support member 110 may be configured to expand radially and/or axially with respect to the opening 190 in one or more directions. For example, the support member 110 may increase in dimension(s) (e.g., cross-sectional height (h) and/or width (w)), cross-sectional area and/or volume prior to or during use, such as, for example, increasing from a first size or volume to a second size or volume, such as, for example, by inflation, mechanically, or by any other means.

In some embodiments, the support member 110 may have an outer periphery or circumference 112 and an inner periphery or circumference 115. The outer periphery or circumference 112 and the inner periphery or circumference 115 may be collectively referred to as the periphery or circumference of the support member 110. In some embodiments, the support member 110, defined by the outer periphery 112, may have a round shape, such as a circular or annular shape (e.g., with respect to the traverse (t) axis). In some embodiments, the support member 110, defined by the outer periphery 112, may have a different shape.

In some embodiments, the inner periphery 115 may surround the opening 190. The inner periphery 115 may define the shape of the opening 190. As shown in the figures, the opening 190 may be disposed offset with respect to the center (C) of the support member 110, defined by the outer periphery 112, so as not to be in the center of the support member 110 defined by the outer periphery 112 (with respect to the transverse (T) axis).

In some embodiments the inner periphery 115 or the opening 190 may have a round shape, such as a circular or annular shape (with respect to the transverse (T) axis), so that the support member 110 may have a ring-like shape. In some embodiments, the support member 110, the outer periphery 112, the inner periphery 115, and/or the opening 190 may have a different shape, different configuration, among others, or any combination thereof.

In some embodiments, the support member 110 may include an outer surface 116 that includes the outer periphery 112 and the inner periphery 115. The outer surface 116 may include a top surface 111 and a bottom surface 113.

In some embodiments, the device 100 may include a base member 160 that extends from the bottom surface 113 of the support member 110 across the opening 190. The base member 160 may surround or envelope one side of the opening 190. By way of example, the base member 160 may act as a bottom surface of the opening 190.

In some embodiments, the base member 160 may be configured to be non-expandable (e.g., non-inflatable). The base member 160 may include one or more openings 162. The base member 160 may include any number of openings 162 and is not limited to the pattern, number, shape, and/or size shown in the figures. For example, the base member 160 may include one opening 162 that is aligned with the opening 190. The base member 160 may have a cup-like shape. Although the base member 160 is shown in the figures, it will be understood that the base member 160 may be omitted from the device 100.

The opening(s) 162 and/or the opening 190 (if no base member 160) may be configured to allow removal of any bodily fluids (e.g., uterine and/or vaginal secretions) that descend. By allowing drainage of any bodily fluids, the device 100 can be configured to prevent any fluid accumulation.

FIGS. 5A-C show the cross-section of the support member 110 taken along the longitudinal (L) axis, which is perpendicular to the transverse (T) axis. As shown in the figures, the support member 110 may include an internal passage 114 that extends along the periphery of the support member 110. In some embodiments, the internal passage 114 may extend entirely along the periphery. In some embodiments, the internal passage 114 may extend along a part of the periphery of the support member 110.

In some embodiments, the support member 110 may include an inner surface 117 that surrounds the passage 114. The passage 114 may be configured to receive a fluid (e.g., one or more gases, liquids, among others, or any combination thereof) to cause the support member 110 to expand. In some embodiments, the outer surface 116 and the inner surface 117 may define a wall of the support member 110. The wall may have a thickness (t).

In some embodiments, the cross-sections of the support member 110 and/or the passage 114 may have any shape. The support member 110 and/or the passage 114 may have dimensions, such as (cross-sectional) height (h), (cross-sectional) width (w), and/or length (l). In some embodiments, the dimensions of the support member 110 and/or the passage 114 may be described as (cross-sectional) area, which corresponds to (cross-sectional) height (h) and (cross-sectional) width (w), and/or volume, which (cross-sectional) corresponds (h), (cross-sectional) width (w), and length (l) along the periphery.

For example, the cross-section of the passage 114 (defined by the inner surface 117) may have a circular shape, as shown in FIGS. 5A-C. By way of example, if the passage 114 has a circular shape, the cross-sectional width (w) and the cross-sectional height (h) of the passage 114 may refer to the diameter. In other embodiments, the shape of the cross-section of the passage 114 may be different, such as other round shapes, ellipse or oval, as well as other shapes.

In some embodiments, in this example, the overall or total cross-section of the support member 110 (e.g., defined by the outer surface 116 so that the overall or total cross-section includes the passage 114, the inner surface 117 and the outer surface 116) may have a circular shape, as shown in FIGS. 5A-C. By way of example, if the overall or total cross-section of the support member 110 has a circular shape, the cross-sectional width (w) and the cross-sectional height (h) may refer to the diameter. In other embodiments, the total cross-section of the support member 110 may have a different shape, such as other round shapes, ellipse or oval, as well as other shapes.

In some embodiments, the shape and/or dimensions of the support member 110, the shape and/or dimensions of the internal passage 114, and/or the wall thickness (t) may not be uniform along the periphery. For example, the wall thickness (t) may vary along the periphery; the total cross-sectional dimensions (e.g., total cross-sectional height (h) and/or total cross-sectional width (w)), total cross-sectional area, and/or total volume of the support member 110; dimensions (e.g., passage cross-sectional height (h) and/or passage cross-sectional width (w)) of the passage 114, passage cross-sectional area of the passage 114, and/or passage volume of the passage 114 may vary along the periphery; among others; or any combination thereof.

In some embodiments, the support member 110 may include one or more portions disposed along the periphery. The one or more portions may include the internal passage 114 so that the one or more portions are fluidly connected. By way of example, the support member 110 may include one or more portions that have a different volume and/or cross-sectional area by having different passage (114) dimension(s), wall thickness(es) (t), and/or the total dimension(s). For example, the support member 110 may include (i) one or more portions having wall thickness (t) that is larger and the passage 114 having a cross-sectional area (e.g., smaller cross-sectional height (h) and/or width (w)) or volume that is smaller than the other portion(s); and/or (ii) one or more portions having wall thickness (t) that is smaller and the passage 114 having a cross-sectional area (e.g., larger cross-sectional height (h) and/or width (w) (e.g., diameter)) or volume that is larger than the other portion(s). This way, when expanded, the one or more portions that has a smaller wall thickness (t) and/or the larger passage (114) cross-sectional area may be expanded more quickly and be overall larger in one or more directions than the one or more portions that has a larger wall thickness (t) and/or a smaller passage (114) area.

In some embodiments, the one or more portions may include one or more portions that have a different cross-sectional area and/or volume and the same wall thickness (t). By way of example, two portions with the same wall thickness (t) may differ in size (e.g., cross-sectional area) of the passage 114.

In some embodiments, the one or more portions may include one or more portions that have the same length (l)

relative to the periphery and/or same volume, different length (l) relative to the periphery and/or different volume, among others, or any combination thereof.

As shown in the figures, the support member 110 may include a first portion 120 and a second portion 140. By way of example, the second portion may oppose the first portion 120 (with respect to the opening 190). In some embodiments, the support member 110 may include a first mid portion 130 that is between the first portion 120 and the second portion 140, and a second mid portion 150 that opposes the first mid portion 130 (with respect to the opening 190) and is between the first portion 120 and the second portion 140. In other embodiments, the first portion 120 may be disposed in a different position relative to the second portion 140. For example, the first portion 120 may be disposed adjacent to the second portion 140.

In some embodiments, the first portion 120 may have a total (cross-sectional) area that is smaller than a total (cross-sectional) area of the second portion 140. For example, the passage 114 along the first portion 120, which is identified by 122, may have a cross-sectional height (h) and/or a cross-sectional width (w) (e.g., diameter) and/or a cross-sectional area that is smaller than a cross-sectional height (h) and/or a cross-sectional width (w) (e.g., diameter) and/or cross-sectional area of the passage 114 along the second portion 140, which is identified by 142. In some embodiments, the wall thickness (t) along the first portion 120, which is identified by 124, may be thicker or greater than the wall thickness (t) along the second portion 140, which is identified by 144, as shown in FIGS. 5A-C.

In some embodiments, the first mid portion 130 and the second mid portion 150 may be substantially similar. For example, the total cross-sectional dimension(s) (e.g., height (h) and/or width (w) (e.g., diameter)) of the support member 110, the passage cross-sectional dimension(s) (e.g., height (h) and/or width (w) (e.g., diameter)) of the passage 114, and the wall thickness (t) along the mid portions 130, 150 may taper along the respective length (l) of the periphery between the first portion 120 and the second portion 140. In some embodiments, along the mid portions 130, 150 from the second portion 120 to the first portion 140, the total cross-sectional dimension(s) (e.g., height (h) and/or width (w)) and the passage cross-sectional dimensions (e.g., height (h) and/or width (w)) of the passage 114 may taper along the respective length (l) of the periphery from the larger cross-sectional area (e.g., height (h) and/or width (w)) of the second portion 140 to the smaller cross-sectional area (e.g., height (h) and/or width (w)) of the first portion 120, and the wall thickness (t) may taper from a smaller wall thickness (t) (144) of the second portion 140 to a larger wall thickness (t) (124) of the first portion 120 along the respective length (l) of the periphery.

In some embodiments, the support member 110 may have a different configuration, different dimensions, among others, or any combination thereof. For example, the support member 110 may include more or less portions that have different total dimension(s), such as total cross-sectional width (w), total cross-sectional height (h) and/or length (l) along the periphery, different total cross-sectional area and/or different total volume; different wall thickness(es) (t); different passage (114) dimension(s), such as passage cross-sectional width (w), passage cross-sectional height (h) and/or length (l) along the periphery; different passage cross-sectional area, and/or different passage volume; different shape(s); among others; or any combination thereof. For example, the passage (114) cross-sectional dimension(s) and wall thickness (t) may be different and/or the same along one or more portions and/or the same portion of the support member 110. By way of example, the wall thickness 124 may be substantially the same as the wall thickness 144 or the wall thickness 144 may be thinner than the wall thickness 124. The configuration, dimensions, etc., may depend on anatomy in which the support member 110 is to be inserted, the anatomical tissue(s)/organ(s) to be supported, among others, or any combination thereof.

In some embodiments, the device 100 may include an adapter 118 disposed on any one of the one or more portions of the support member 110. As shown in FIGS. 5A, 5B, and 6-8, the adapter 118 may be disposed along the bottom surface 113. By way of example, as shown in these figures, the adapter 118 may be disposed on the second portion 140.

In some embodiments, the adapter 118 may be in communication with the internal passage 114 and configured to cause the support member 110 to expand and/or contract by receiving and/or removing a gas (e.g., air) or fluid (e.g., saline) from the passage 114. The adapter 118 may be configured to removably receive tubing 610 (shown in FIG. 6).

In some embodiments, the adapter 118 may include a two-way valve 119 configured to open to allow the expansion/contraction of the support member 110 and to close to maintain the level of expansion/contraction of the support member 110. In some embodiments, the two-way valve 119 may be a valve that is configured to move between the open and close states based on the position of the valve with respect to the adapter 118. By way of example, the two-way valve 119 may be configured to rotate with respect to the adapter 118, for example, using the tubing 610, to change the state of the valve.

In other embodiments, the adapter 118 may be different. For example, the adapter 118 may include a different valve (e.g., one-way valve, different two-way valve, among others, or any combination thereof), more than one valve, among others, or any combination thereof.

In some embodiments, the support member 110 and/or the base member 160 may be made of one or more flexible materials. The material(s) may include any one or more flexible materials that is bio-compatible, non-absorptive, and resists bacterial growth. For example, the material may include silicon, santropene, among others, or any combination thereof. By using a flexible material, the support device 100 may be easily inserted and positioned within the vaginal canal.

In some embodiments, the support device 100 may be molded or manufactured as a single device. In other embodiments, the components of the device 100 may be separately molded or manufactured.

In some embodiments, the device 100 may include a flexible plastic or metal coil incorporated within the flexible material. For example, a spring may be incorporated within the support member 110 and/or the base member 160 to exert additional pressure, for example, against the vaginal walls.

In some embodiments, the outer surface(s) of the support device 100 may be smooth. In some embodiments, the outer surface(s) of the support member 110 and/or the base member 160 may be textured or roughened along a portion or the entire surface. For example, the outer surface(s) of the support member 110 and the base member 160 may include grooves, divots, barbs, among others, or any combination thereof.

In some embodiments, the support device 100 may be configured to elute a therapeutic agent or substance, for example, for treatment or for preparation of insertion of the device 100. By way of example, the support member 110 and/or the base member 160 may include a coating or a material that can elute the therapeutic agent or substance.

As shown in FIG. 6, the system 600 may include the support device 100 and the tubing 610 that is configured to connect to the adapter 118. In some embodiments, the tubing 610 may include an adapter (not shown) on the opposite end to removably connect to an expansion device configured to cause at least expansion of the support member. For example, the expansion device may include but is not limited to an air pump 910 (e.g., as shown in FIGS. 9 and 10), a syringe of an expansion fluid (e.g., saline solution), among others, or any combination thereof.

In some embodiments, the tubing 610 may be made of one or more one or more flexible materials that is bio-compatible, non-absorptive, and resists bacterial growth. In some embodiments, the tubing 610 may be configured to remain in the patient after the device 100 insertion, to allow for further adjustment during the course of treatment (e.g., expansion/contraction depending on use and need).

FIG. 7 show a view 700 of the device 100 in its resting, contracted (non-expanded) state with tubing 610 connected to the adapter 118. FIGS. 1-6 show the support member 110 and/or the device 100 in its resting, contracted (non-expanded state). In this state, the device 100 may be flexible and be able to be collapsed for insertion.

FIG. 8 shows the view 800 of the device 100 in an expanded state due to the delivery of a fluid 810 via the tubing 610 through the adapter 118 into the passage 114. As shown in this figure, the internal passage 114 of the support member 110 can expand thereby causing the overall or total dimensions (e.g., total cross-sectional height (h) and/or total cross-sectional width (w) and/or length (l) of periphery) of the support member 110 to increase in size resulting in the volume of the support member 110 to increase. The directions of the expansion and the level of expansion may depend on the anatomy in which the system 100 is implanted. The level of expansion of the second portion 140 can be greater than the level of expansion of the first portion 120 (e.g., in any state of expansion), for example, due to the corresponding size/dimension(s) of the internal passage 114. The rate of expansion of the second portion 140 can also be faster than the rate of expansion of the first portion 120 due to the difference in the corresponding wall thickness (t). Also, as shown in FIG. 8, the base member 160 may not expand when the support member 110 is expanded.

Figure 9A:
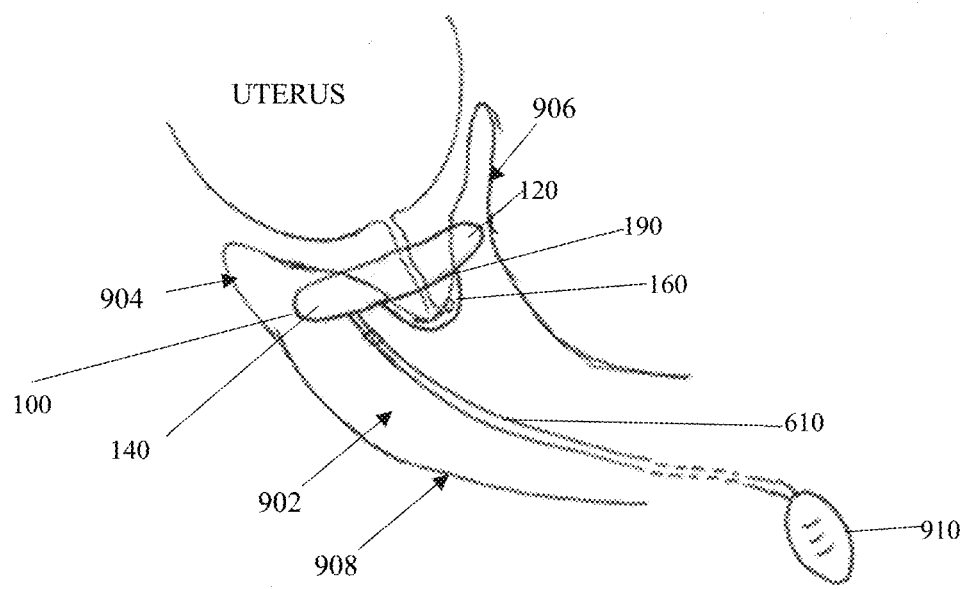
FIGS. 9A and 9B show methods of delivering the anatomical support system according to embodiments.
Figure 9B:
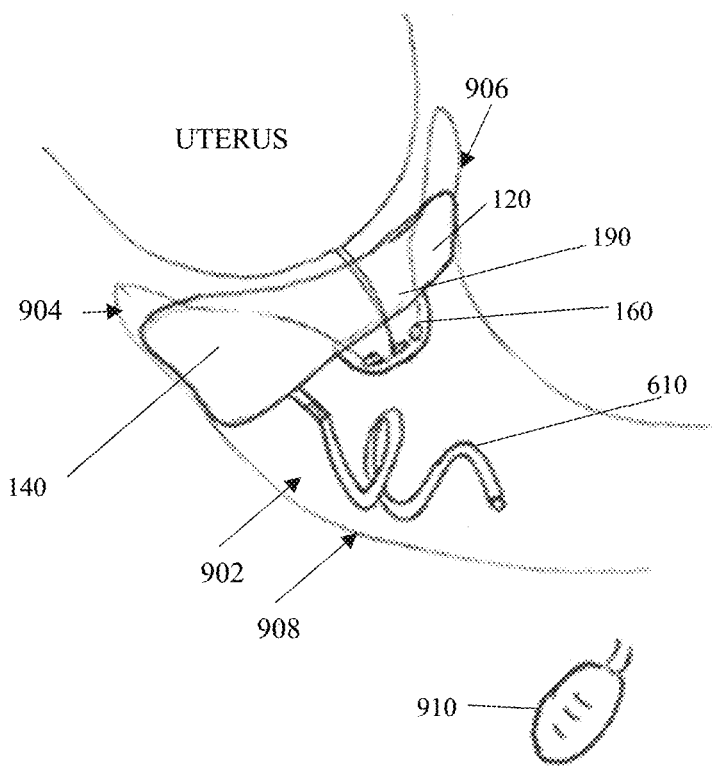

FIGS. 9A and 9B show an example of delivering the device 100 shown in FIGS. 1-8 into the vaginal canal to support the cervix. FIG. 9A shows a view 900 showing the placement of the device 100 before being expanded. As noted above, the device 100 may be folded or collapsed during insertion before it is placed within the vaginal canal 902. As shown in FIG. 9A, the device 100 may be placed so that the second portion 140 is adjacent to the posterior fornix 904 and the first portion 120 is adjacent to the anterior fornix 906. The opening 190 and/or the base member 160 may be placed so as to surround the cervix. The opening(s) 190 and/or 162 may be configured to allow any uterine and/or vaginal secretions to drain out of the device 100. This way, fluid accumulation can be prevented.

After placement, the clinician and/or patient can cause the support member 110 to expand by delivering a fluid until the device 100 is anchored in place and supports the cervix (or other anatomical structure). In this example, the clinician and/or patient can use an expansion device (e.g. a hand pump) 910 to deliver air to the passage 114 of the support member 110 via the tubing 610 and the adapter 118 (in the open state).

After the support member 110 is expanded to support the anatomical structure (e.g., cervix/vagina) and the adapter 118 is moved to the closed state, the expansion device 910 can be detached. FIG. 9B shows a view 950 showing the device 100 in expanded state with the expansion device 910 removed. As shown in this view, in the expanded state, the device 100 can be positioned against the vaginal wall 908 to support the cervix. In the expanded state, the device 100 may also be configured to support other tissues or others, such as pelvic, vaginal, bladder, and/or rectal. The first portion 120 can be anchored in place even though it is structured to expand less due to the size of the anterior fornix region 906. The second portion 140 can be anchored against the vaginal wall 908 because it has expanded to sufficient size to fill the posterior fornix 904. The inward expansion of the support member 110 (towards the opening 190) can force the cervix to close, as shown in FIG. 9B. The tubing 610 can be detached from the expansion device 910 and remain in the canal 902. For example, the tubing 610 can be folded and stored into the canal so that it can be easily accessed for further adjustment to the device 100 without affecting the daily function.

For example, as the pregnancy progresses, the device 100 may be adjusted, for example, by adjusting the level of expansion. If, for example, the clinician and/or patient needs to further expand the support member 110, the clinician and/or patient may (i) retrieve and/or attach the tubing 610 and (ii) attach the tubing 610 to an expansion device (e.g., the pump 910) and cause the support member 110 to expand. The support member 110 may also be enabled to allow the expansion by causing the valve (e.g., the valve 119) at the adapter 118 to open, for example, by rotating the tubing 610 to cause the valve to move to the open position relative to the adapter 118. After which, the clinician and/or patient may use the expansion device 910 to deliver air via the tubing 610 and the passage 114 to cause the member 110 to further expand.

By way of another example, if the clinician/patient needs to reduce the level of expansion and/or remove the device 100, the clinician/patient may cause the adapter 118 to remove the fluid, for example, by causing the valve to move to an open position. For example, the clinician/patient may rotate the tubing 610 to cause the valve to move to the open position relative to the adapter 118 to release an amount or all of the fluid contained within the passage 114. If the clinician/patient wants to remove the device 100, after the support member 110 is contracted to its resting state (e.g., substantially all of the air/fluid is released from the passageway), the device 100 may be removed (e.g., for example can be folded or collapsed after moved away from the cervix).

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. An anatomical support device, comprising:
   an opening; and
   a support member having a periphery that surrounds the opening;

the support member being configured to releasably and adjustably expand between one or more expanding states from a resting state and contract to the resting state; and the support member including:
an internal passage that extends along the periphery;
one or more portions disposed along the periphery, the one or more portions including:
a first portion disposed along the periphery, the internal passage along the first portion having a first passage cross-sectional area, the first portion having a first wall thickness along the periphery; and
a second portion disposed along the periphery, the internal passage along the second portion having a second passage cross-sectional area, the second portion having a second wall thickness along the periphery;

wherein the first wall thickness and/or the first passage cross-sectional area is different from the second wall thickness and/or the second passage cross-sectional area;

wherein the first wall thickness is greater than the second wall thickness; and wherein the second portion is larger than the first portion when expanded.

2. The device according to claim 1, further comprising:
a base member that protrudes from the support member and envelopes the opening.

3. The device according to claim 2, wherein the base member includes one or more openings.

4. The device according to claim 2, wherein the base member is structured to be non-expandable.

5. The device according to claim 1, wherein the support member further includes one or more mid portions disposed between the first portion and the second portion.

6. The device according to claim 1, wherein the second portion is structured to expand faster than the first portion when expanding to the one or more expanded states.

7. The device according to claim 1, further comprising:
an adapter disposed on one portion of the one or more portions;
the adapter being in communication with the internal passage and configured to receive tubing; and
the adapter including a valve, the valve being configured to open so that the support member expands and/or contracts and to close so that the support member maintains the one or more expanding states and/or the resting state.

8. The device according to claim 1, wherein the support member has a center relative to the periphery and the opening is disposed offset from the center.

9. The device according to claim 1, wherein:
the internal passage is configured to receive a fluid; and
the one or more expanded states is based on the amount of fluid disposed within the internal passage.

10. The device according to claim 1, wherein the support member is made of one or more flexible materials.

11. The device according to claim 1, wherein the support member is structured to be collapsible when the support member is in the resting state.

12. The device according to claim 1, wherein:
the first passage cross-sectional area is smaller than the second passage cross-sectional area; and the second portion is larger than the first portion when in the one or more expanded states.

13. The device according to claim 1, wherein:
the first passage cross-sectional area is defined by a first passage cross-sectional height and a first passage cross-sectional width and the second passage cross-sectional area is defined by a second passage cross-sectional height and a second passage cross-sectional width; and
the first passage cross-sectional height and/or first passage cross-sectional width is different from the second passage cross-sectional height and/or the second passage cross-sectional passage width.

14. An anatomical support device, comprising:
an opening; and
a support member having a periphery surrounding the opening, the periphery including an outer surface and an inner surface;
the support member being configured to releasably and adjustably expand between one or more expanding states from a resting state and contract to the resting state; and
the support member including:
an internal passage disposed along the periphery, the inner surface surrounding the internal passage;
a wall thickness defined by the outer surface and the inner surface; and
one or more portions disposed along the periphery, the one or more portions including:
a first portion disposed along the periphery, the first portion having a first cross-sectional area, the first cross-sectional area including a first wall thickness and a first passage cross-sectional area; and
a second portion disposed along the periphery, the second portion having a second cross-sectional area, the second cross-sectional area including a second wall thickness and a second passage cross-sectional area;

wherein the first cross-sectional area is different from the second cross-sectional area;

wherein the first portion and the second portion are structured to expand to a different size when expanded in each of the one or more expanding states;

wherein the support member has a center relative to the periphery and the opening is disposed offset from the center;

wherein the first wall thickness is greater than the second wall thickness; and wherein the second portion has a larger cross-sectional area than the first portion when expanded.

15. The device according to claim 14, wherein:
the first cross-sectional area is based on a first cross-sectional height and a first cross-sectional width;
the second cross-sectional area is based on a second cross-sectional height and a second cross-sectional width; and
the first cross-sectional height and/or the first cross-sectional width is smaller than the second cross-sectional height and/or the second cross-sectional width.

16. The device according to claim 14, further comprising:
a base member that protrudes from the outer surface and envelopes the opening.

17. The device according to claim 16, wherein:
the base member includes one or more openings; and
the base member is structured to be non-expandable.

* * * * *